United States Patent [19]
Nanci et al.

[11] Patent Number: 5,824,651
[45] Date of Patent: Oct. 20, 1998

[54] PROCESS FOR MODIFICATION OF IMPLANT SURFACE WITH BIOACTIVE CONJUGATES FOR IMPROVED INTEGRATION

[75] Inventors: Antonio Nanci, Dollard-des Ormeaux; Marc D. McKee, Pointe-Claire; Edward Sacher, Côte-St-Luc; Oumarou Savadogo; James Wuest, both of Montréal, all of Canada

[73] Assignee: Universite de Montreal, Quebec, Canada

[21] Appl. No.: 672,243

[22] Filed: Jun. 28, 1996

Related U.S. Application Data

[63] Continuation of Ser. No. 322,998, Oct. 14, 1994, abandoned, which is a continuation-in-part of Ser. No. 226,345, Apr. 12, 1994, abandoned, which is a continuation-in-part of Ser. No. 58,753, May 10, 1993, abandoned.

[51] Int. Cl.⁶ .......................... A61K 38/18; A61K 38/39; A61F 2/28; B05D 3/04
[52] U.S. Cl. .................. 514/21; 427/2; 427/327; 427/337; 427/338; 530/350; 530/395; 530/402; 204/129.95; 106/124; 623/16; 514/12
[58] Field of Search .................. 427/2, 327, 337, 427/338; 530/395, 350, 402; 204/129.95; 106/124; 514/12, 21; 623/16

[56] References Cited

U.S. PATENT DOCUMENTS

| | | | |
|---|---|---|---|
| 4,038,702 | 8/1977 | Sawyer | 3/1.5 |
| 4,336,618 | 6/1982 | Raab | 3/1.913 |
| 4,365,359 | 12/1982 | Raab | 3/1.912 |
| 4,372,831 | 2/1983 | Rosswag | 204/129.8 |
| 4,652,459 | 3/1987 | Engelhardt | 427/2 |
| 4,788,176 | 11/1988 | Wieserman et al. | 502/104 |
| 4,795,475 | 1/1989 | Walker | 623/66 |
| 4,973,493 | 11/1990 | Guire | 427/2 |
| 4,979,959 | 12/1990 | Guire | 623/66 |
| 5,045,318 | 9/1991 | Tengvali et al. | 424/422 |
| 5,152,993 | 10/1992 | Bjursten et al. | 424/422 |
| 5,205,921 | 4/1993 | Shirkanzadeh | 205/318 |
| 5,211,663 | 5/1993 | Kovacs et al. | 623/16 |
| 5,217,492 | 6/1993 | Guire et al. | 623/11 |
| 5,263,992 | 11/1993 | Guire | 623/66 |
| 5,344,425 | 9/1994 | Sawyer | 606/198 |
| 5,350,800 | 9/1994 | Verhoeven et al. | 525/54.2 |

FOREIGN PATENT DOCUMENTS

| | | |
|---|---|---|
| A-0 109 061 | 5/1984 | European Pat. Off. |
| WO-A-9000887 | 2/1990 | WIPO |

OTHER PUBLICATIONS

Volmer–Uebing et al., Applied Surface Science, vol. 55, pp. 19–35, 1992.
Sukenik et al., J. Biomed. Materials Res., vol. 24, pp. 1307–1323, 1990.
Stanford et al, J. Dent. Res., 73(5):1061–1071, 1994.

Primary Examiner—Chhaya D. Sayala
Attorney, Agent, or Firm—Evenson, McKeown, Edwards, & Lenahan, PLLC

[57] ABSTRACT

The present invention relates to a process for the covalent coating of implants with a bioactive conjugate, which comprises the steps of: a) cleaning a metal implant surface from contaminants by deoxidation with potentiostatic electrochemical polishing in a solution selected from ethanol, perchloric acid-butanol-methanol solution, $H_2O_2$—NaCl—$NaH_2PO_4$ or by chemical cleaning with a solution selected from the group consisting of $HF/HNO_3$, $H_2O_2/H_2SO_4$ and $H_2O_2/KOH$; b) coating the cleaned implant surface of step a) with a bioactive conjugate, wherein the conjugate has the following structural Formula I:

$$—R—X—P \qquad I$$

wherein, R is O or S, adapted to be covalently attached to an implant surface; X is selected from a bond, linear or branched chains of 1 to 30 covalently attached atoms of at least C, N, O, Si or S, rings of 1 to 20 covalently attached atoms of at least C, N, O, Si or S, and a combination thereof; and P is a bioactive molecule moiety which promotes tissue growth, stabilization and integration, and wherein the moiety retains its biological activity.

19 Claims, 9 Drawing Sheets

PROCESS FOR MODIFICATION OF IMPLANT SURFACE WITH BIOACTIVE CONJUGATES FOR IMPROVED INTEGRATION

RELATED APPLICATION

This application is a continuation of application Ser. No. 08/322,998 filed on Oct. 14, 1994, now abandoned, which is a continuation-in-part of application Ser. No. 08/226,345 filed on Apr. 12, 1994, abandoned, which is a continuation-in-part of application Ser. No. 08/058,753 filed on May 10, 1993, abandoned.

BACKGROUND OF THE INVENTION (a) Field of the Invention

The invention relates to a process for the covalent attachment of bioactive conjugates to an implant surface for improving its integration into surrounding tissues.

(b) Description of Prior Art

Devices in the form of plates, nails, pins, screws, and specially formed parts are commonly implanted into the skeletal structure of humans as artificial prosthetic means for permanent replacement of missing structural parts, or as permanent anchoring devices for maintaining a fixed relationship between the portions of a fractured bone. Clearly, in those situations where durability is necessary or desirable, the implanted part should remain permanently adhered to the contacting bone surface. This requirement has been a source of some difficulty in the past, where prosthetic parts composed of high strength materials such as titanium, stainless steel, tantalum, or Vitallium™ (an alloy of cobalt, chromium, and molybdenum) have generally been found incapable of forming a strong union with the natural bone structure into which the implantation is made. Highly magnified photographs of sections taken through bone and implant where failure has occurred have revealed what appears to be an absence of coalescence between the artificial and natural parts, and in fact an actual separation between the implant surface and the bone matter adjacent thereto is often apparent.

The use of surgical prosthetic devices, otherwise known as implants, is well known in various surgical applications, such as reconstructive surgery, for example, in the replacement of hip joints or the like. These applications generally involve the use of an implant constructed of metal or alloy which is not substantially corroded or otherwise degraded by body fluids. These prior implants, however, suffer from a number of limitations.

Typically, in the setting of broken bones, metal plates have been used which are secured to either side of the bone fracture. The plates are commonly secured to the bones by screws. While the plate in time becomes encapsulated in bone and body tissue, no bond is formed between the implant and the tissue. If one of the screws comes loose, the patient may have to undergo additional corrective surgery.

Suggestions have been made in the prior art to provide surgical prosthetic devices which are capable of permanent incorporation into the body, usually the bone, with bonding between the implant and the tissues.

In one prior suggestion, there is described a prosthetic device consisting of a metal substrate or base having a thin porous coating of metal overlying and bonded to the surface. The presence of the pores allows the soft or hard tissue to grow into the porous coating of the device and hence achieve mechanical incorporation into the body.

The only method of forming the coating which is described in this prior art suggestion is the technique of plasma or flame spraying onto the metal substrate. The result of this process is a densely adherent layer of the sprayed metal on the substrate metal with no porosity or practically no porosity at the interface between the coating and the substrate and with gradually increasing porosity, including increasing pore size and decreasing density, from the interface to the surface of the coating.

While this technique may be effective in providing a porous coating on a metal substrate, nevertheless the technique results in a very serious drawback in the finished prosthetic device. In tests designed to show the ingrowth of tissue into the coated surface of the device, a pin, having the coating thereon, and after embedding in a bone for a period of time, was subjected to a pull-out test. This pull-out test resulted in shearing at the interface between the coating and the base metal. This result indicates that the overall strength of the device is less than that of the bone. Quite clearly, the provision of a device weaker than the bone to which it is attached could result in failure of the device due to shearing at the interface with harmful and painful consequences for a patient who is treated using such a device.

Another prior art suggestion involves the provision of a prosthetic device constructed of porous ceramic material. This material is structurally weak and attempts to overcome this defect by filling the bulk of the device with resin material, leaving a porous surface area. Although the presence of the resin may increase the strength of the central portion of the device, the surface region remains weak. Further, the presence of resin material degradable by body fluids would lead to unsatisfactory use in the human body. In addition, the maximum pore size for the ceramic is indicated to be 50 microns, and much smaller sizes are preferred. If the pore size were greater than 50 microns, then the structure would become too weak for effective use.

It has been known to anchor surgical implants in bones with the use of cements. It has also been known to improve the anchorage of an implant without using a cement by constructing the implant so as to receive an ingrowth of bone tissue. For example, implants have been provided with a porous surface of a certain depth. However, these porous surface implants have not proven themselves in practice since the mechanical strength of the anchoring surface is greatly affected in an adverse sense. The reason for this weakening of the material is that the pores produce sharp corners and edges in the material. This leads, especially in the case of long-term alternating stresses, to cracks which continue into the solid core of the implant and eventually to fatigue fractures.

Implants have also been constructed with a regular arrangement of bosses and/or depressions in order to improve mechanical adhesion within bones. However, quite apart from the fact that sharp corners and edges have not been avoided in these structures, increased adhesion between the implants and the tissue has not been achieved. This latter failure has occurred because only an insufficient increase of the surface is obtained. As is known, an increase in the anchoring surface is a decisive feature which can influence and improve a bond between the tissue and the anchoring part of the implant which acts as a foreign body therein.

U.S. Pat. No. 3,605,123 in the name of Hahn (Apr. 29, 1969) describes a prosthesis of high structural strength, with a capability of promoting substantially complete integration with the bone structure in which it is implanted.

U.S. Pat. No. 3,855,638 in the name of Pilliar (Dec. 24, 1974) describes a surgical prosthesis of a composite structure consisting of a solid metallic material substrate and a porous coating adhered to and extending at least partially over the surface of the substrate. The porous coating on the surface of the substrate has several parameters which are essential to the provision of a satisfactory device free from the defects of the prior devices.

U.S. Pat. No. 4,272,855 in the name of Frey (Jun. 16, 1981) describes a bone implant with an anchoring surface including a plurality of villi.

However, none of these prior art implants is provided with a chemical coating which would promote a chain of biochemical reactions at the tissue-implant interface, thereby promoting tissue growth, stabilization and integration of the implant.

Substantial progress has been made with regard to implants such as for the restoration of oral tissues, and currently employed techniques rely principally on the use of alloplastic replacement materials. Titanium, titanium-alloy and hydroxyapatite-coated orthopedic and dental implants are widely used in medicine and dentistry for tissue repair, reconstruction and replacement, and as supports for various prostheses. These implants are generally utilized in surgical procedures involving bone, where they are incorporated into this hard, mineralized tissue ('osseointegration'), and in some cases, also traverse soft tissue such as skin or the mucosa of the oral cavity.

In hard biological structures such as teeth (dentin, cementum) and bone, great rigidity and strength are imparted to these tissues by an extensive network of collagen protein fibers that are impregnated with apatitic mineral. Although collagen is by far the most abundant protein in these tissues, other non-collagenous proteins are also secreted by cells and accumulate within their respective extracellular matrices. Although the exact function of these non-collagenous proteins is unknown, they have recently come under intense scrutiny since experimental results indicate that they may play a critical role in the initiation and regulation of calcification (reviewed by Boskey, *Bone Mineral,* 6:111–123, 1989 and Gorski, *Calcif. Tissue Int.,* 50:391–396, 1992).

One group of non-collagenous proteins, the phosphoproteins (containing organic phosphorus), and more specifically a dentin phosphoprotein called phosphophoryn and two bone phosphoproteins named osteopontin and bone sialoprotein (reviewed by Butler, *Connect. Tissue Res.,* 23:123–136, 1989 and Butler, *J. Biol. Buccale,* 19:83–89, 1991), may participate by acting as a seed or regulator of mineral crystal growth and/or by directing cells and their associated functions to specific sites within the tissue. In addition to its co-localization with mineral at early sites of calcification, osteopontin and bone sialoprotein are known to contain the Arg-Gly-Asp (RGD) cell-binding peptide sequence that binds to a plasma membrane integrin receptor and promotes cell attachment (see *Telios Pharmaceuticals, Inc., Manual for Summary:*1–10). The presence of this triplet sequence, the distribution of these proteins, and their association with mineral, suggest that these phosphoproteins may have a multifunctional role during mineralized tissue formation whereby they may, firstly, initiate and regulate mineralization, and secondly, direct dynamics by mediating cell attachment to the matrix (McKee et al., *Anat. Rec.,* 234:479–492, 1992 and McKee et al., *J. Bone Miner. Res.,* 8:485–496, 1992).

For an implant to be successful, the intraosseous portion of the implant must undergo osseointegration and a functional junctional epithelium-like seal must form around the transgingival portion (reviewed by McKinney et al., *J. Dent. Educ., (Sp. Iss.)* 52:696–705, 1988). Any imperfection in these events may lead to the eventual rejection of the implant. The junctional epithelium, in normal conditions, seals the subgingival portion of the tooth from the buccal environment and consists of an epithelial layer, a glycoproteinaceous structure which resembles a basal lamina, and hemidesmosomes (Schroeder, *Differentiation of human oral stratified epithelia,* S. Karger Publishers, Basel., 1981). The basal lamina and the hemidesmosomes are believed to serve in the attachment of the gingiva to the tooth surface (Schroeder, *Helv. Odont. Acta,* 13:65–83, 1969), possibly via integrin receptors (Hormia et al., *J. Dent. Res.,* 71:1503–1508, 1992). It has been suggested that laminin (Sawada et al., *J. Perio. Res.,* 25:372–376, 1990) and collagen type VIII (Salonen et al., *J. Perio. Res.,* 26:355–360 1991) are present in the junctional epithelium, the presence of the latter being particularly interesting in that collagen type VIII is not a common component of basement membranes in general. Similarly, the sugar content of the junctional epithelium basal lamina, as visualized by lectin-gold cytochemistry (Zalzal et al., *J. Dent. Res.,* 72:411, 1993), appears to be unique. Just like conventional basement membranes, the basal lamina of the junctional epithelium could play an inductive role in the specialization of the oral epithelium to become bona fide junctional epithelium (reviewed by Timpl, *Eur. J. Biochem.,* 180:487–502, 1989).

The fundamental assumption in each of these situations is that extracellular matrix components of the adjacent tissue (i.e. bone, soft connective tissues or epithelium) allow 'bonding' between the non-biological implant and the biological extracellular matrix surrounding the implant. In bone, for example, this bonding region (interface) has been identified, using electron microscopy, as a layer of non-collagenous organic material separating the bone matrix proper from the implant (Steflik et al., *J. Biomed. Materials Res.,* 26:529–545, 1992).

Sukenik, C. N. et al. (*J. Biomed. Materials Res.,* 24:1307–1323, 1990) describes the modulation of cell adhesion by modification of titanium surfaces with covalently attached self-assembled monolayers. However, they do not show the attachment of bioactive conjugates which include biologically active molecules able to promote tissue growth, stabilization and integration at the tissue-implant interface.

U.S. Pat. No. 4,038,702 in the name of Sawyer et al. (Aug. 2, 1977) teaches the treatment of a metal surface to obtain a negative surface potential by chemical polishing, electrochemical polishing or cathodic treatments in an acid or alkaline bath. None of these procedures produces a chemically clean surface free of impurities. Moreover, none of the electrolytes referred thereto could be used for the cleaning of a titanium implant surface. The chemical composition of the electrolytes, the current and the temperature used would not be operative for the cleaning of an implant surface in accordance with the present invention, where a trace of contaminants may have tremendous effects on the coating. The processes taught in this patent result in chemically modified metal surface having a negative surface charge wherein contaminants have been intentionally deposited from the solution to the metal surface to result in a negative charge. Thus, the resulting metal surfaces have low degrees of contamination.

U.S. Pat. No. 4,652,459 in the name of Engelhart (Mar. 24, 1987) teaches the cleaning of implant surfaces through several steps, such as with perchloric acid. The implants used in this process are made of metal, particularly highduty or refined steel, coated with a layer of glass or enamel. The electrolyte solutions used are not adapted for the electrochemical cleaning of titanium surfaces in accordance with the present invention. Accordingly, this cleaning process is not appropriate for cleaning metal implants and would leave contaminants, such as Ti oxides and carbides. In addition, the coatings are applied to the layer of glass or enamel and not directly to the surface of the metal.

U.S. Pat. No. 4,372,831 in the name of Rosswag (Feb. 8, 1983) teaches the use of electrolyte solutions for electrochemical polishing which include perchloric acid. The electrochemical polishing conditions, such as the electrolyte solutions, temperature, current and voltage taught in this patent are not suitable for the cleaning of titanium surfaces. Further, this cleaning process would leave a layer of phosphate and $TiO_2$ contaminants at the implant surface.

U.S. Pat. No. 5,217,492 in the name of Guire et al. (Jun. 8, 1993) teaches the use of a spacer having one end which can covalently bond to a surface such as an implant surface and the opposite end which can be covalently attached to a biomolecule. The covalent spacer taught therein does not result in permanent attachment to metal surfaces, such as titanium, and it does not produce modified metal surfaces that would be stable under physiological conditions. Moreover, the use of silanes for covalent attachment to surfaces is not discussed.

Stanford et al. (*J. Dent. Res.*, 73(5):1061–1071, 1994) discloses that bone cell expression on titanium surfaces is altered by sterilization treatments. It is demonstrated in this article that the biological activity of biomolecules coating a titanium implant surface is easily affected by different sterilization conditions. It is thus not easy to arrive at a cleaning process which would give an implant surface free of contaminants. It does not consider the potentiostatic cleaning of titanium surfaces. In any case, there is not disclosed a cleaning process which would greatly enhance the covalent attachment of biomolecules to the implant surface.

It would be highly desirable to have a cleaning process for metal implants which would result in a cleaned surface without any contaminants and which would greatly enhance the covalent attachment of biomolecules to the implant surface.

It would be highly desirable to have a chemical coating for metal implants which would mimic the biological activity of the natural proteins found at the tissue-implant interface in the healing patient with an integrated implant, based on normally-occurring biochemical and physiological mechanisms.

It would be highly desirable to have a chemical coating for metal implants which would promote a chain of biochemical reactions at the tissue-implant interface, thereby promoting tissue growth, stabilization and integration of the implant.

It would be highly desirable to provide a process for the long term coating of metal implants with chemical compounds in such a way that the coating remains intact under physiological conditions.

SUMMARY OF THE INVENTION

One aim of the present invention is to provide a chemical coating for metal implants which would mimic the biological activity of the proteins found at the tissue-implant interface in the healing patient with an integrated implant, based on normally-occurring physiological mechanisms.

Another aim of the present invention is to provide a bioactive conjugate which would promote a chain of biochemical reactions at the tissue-implant interface, thereby promoting tissue growth, stabilization and integration of the implant.

Another aim of the present invention is to provide a process for the covalent coating of implants with a bioactive conjugate.

In accordance with the present invention there is provided a bioactive conjugate adapted to coat a metal implant outer surface which has the following structural formula I:

wherein,

R is O or S, adapted to be covalently attached to an implant surface;

X is selected from a bond, linear or branched chains of 1 to 30 covalently attached atoms selected from the group consisting of C, N, O, Si or S or other linking atoms, rings of 1 to 20 covalently attached atoms selected from the group consisting of C, N, O, Si or S or other linking atoms and a combination of rings and chains of similar composition; and P is a covalently-attached bioactive molecule moiety which promotes tissue growth, stabilization and integration, and wherein the moiety retains its biological activity.

More particularly, in accordance with the present invention, X is selected from one of the following possibilities: a direct bond to a bioactive molecule; a linear alkyl $C_1$–$C_{30}$ chain, terminated by COOH, $NH_2$, OH, SH or other functional groups chosen to permit covalent linking to a bioactive molecule; a linear chain consisting of 1–20 atoms of C interspersed with 1–10 atoms of N, O or S, terminated by COOH, $NH_2$, OH, SH or other functional groups chosen to permit covalent linking to a bioactive molecule; a linear alkylsilyl $SiC_1$–$SiC_{30}$ chain, terminated by COOH, $NH_2$, OH, SH or other functional groups chosen to permit covalent linking to a bioactive molecule; or rings composed of C and/or N, connected directly to a bioactive molecule or connected by means of linear chains of C, N, O or S atoms, terminated by COOH, $NH_2$, OH, SH or other functional groups chosen to permit covalent linking to a bioactive molecule.

The X moiety of the bioactive conjugate is selected depending on the desired P moiety which is to be attached to an implant and is chosen according to the desired spacing distance of the P moiety from the implant.

The preferred X moieties in accordance with the present invention are $C_2$–$C_{12}$ alkyl, which may be substituted or non-substituted, $SiC_3$–$SiC_{12}$, which may be substituted or non-substituted, and 1,3,5-triazine (cyclic $C_3N_3$), which may be substituted or non-substituted.

The X moiety may be substituted with a substituent selected from the group consisting of COOH, $NH_2$, OH, SH, Cl or other groups chosen to permit covalent linking to a bioactive molecule.

In accordance with the present invention there is provided a bioactive conjugate adapted to coat a metal implant outer surface.

Further, the bioactive conjugate of the present invention may be capable of forming a self-assembling monolayer on the implant surface.

The coating of the metal implant in accordance with the present invention, in addition to covalently attaching the bioactive molecule moiety which promotes tissue growth, stabilization and integration onto the implant surface, inhibits the contamination of the metal implant surface.

More particularly, in accordance with the present invention, P is selected from normal and/or derivatised osteopontin, bone sialoprotein, bone acidic glycoprotein-75, osteocalcin, osteonectin, bone morphogenetic proteins, transforming growth factors, laminin, type IV collagen, type VIII collagen, enamel proteins (amelogenins and non-amelogenins), $\alpha_2$HS-glycoprotein, fibronectin, cell adhesion peptides, prostaglandin, serum proteins, glucocorticosteroids (dexamethasone), phosphate, phosphoserine, pyrophosphates, phosphothreonine, phosvitin, phosphophoryn, biphosphonates, phosphonates, phosphatases, sulfonates, sulfates, carboxy group, bone and epithelial proteoglycans, mineral and cell binding peptide sequences such as Arginine-Glycine-Aspartic acid (Arg-Gly-Asp), polyaspartate, and other biological molecules capable of promoting tissue integration, and non-biological molecules chosen to imitate these effects.

In accordance with the present invention the expression "metal implant" is intended to mean any surgical implants made of solid metal or of a metal sheet or foil, or an implant having at least one side or one surface coated with metal.

More particularly, in accordance with the present invention, the metal implant is made of titanium, stainless steel, tantalum, Vitallium™ or any other medically acceptable metallic implant material.

In accordance with the present invention there is provided a process for the covalent coating of implants with a bioactive conjugate, which comprises the steps of: a) cleaning a metal implant surface from contaminants by chemical cleaning in HF—HNO$_3$ followed by deoxidation with potentiostatic electrochemical polishing in a solution selected from ethanol, perchloric acid-butanol-methanol solution, H$_2$O$_2$—NaCl—NaH$_2$PO$_4$ or by chemical cleaning with a solution of hydrogen peroxide and sulfuric acid; and b) coating said cleaned implant surface of step a) with a bioactive conjugate.

In accordance with the present invention there is also provided a process for the covalent coating of implants with a bioactive conjugate, which comprises the steps of: a) cleaning a metal implant surface from contaminants by chemical cleaning in HF—HNO$_3$ followed by deoxidation with potentiostatic electrochemical polishing in a solution selected from ethanol, perchloric acid-butanol-methanol solution, H$_2$O$_2$—NaCl—NaH$_2$PO$_4$ or by chemical cleaning with a solution of hydrogen peroxide and sulfuric acid; b) deoxidizing the cleaned metal implant surface of step a) in medium; and c) coating said deoxidized implant surface of step b) with a bioactive conjugate of the present invention.

In accordance with the present invention there is also provided a process for the covalent coating of implants with a bioactive conjugate, which comprises the steps of: a) cleaning a metal implant surface from contaminants by chemical cleaning in HF—HNO$_3$ followed by deoxidation with potentiostatic electrochemical polishing in a solution selected from ethanol, perchloric acid-butanol-methanol solution, H$_2$O$_2$—NaCl—NaH$_2$PO$_4$ or by chemical cleaning with a solution of hydrogen peroxide and sulfuric acid; b) deoxidizing the cleaned metal implant surface of step a) in medium; c) controlled re-oxidation of the deoxidized metal implant surface of step b); and d) coating the implant surface of step c) with a bioactive conjugate of the present invention under conditions causing covalent coating of the implant surface.

The term "coating" is intended to mean that a preformed bioactive conjugate of the present invention may be covalently attached to the implant surface in one step or in several steps using a suitable compound which may be subsequently connected to a bioactive molecule to form a bioactive conjugate.

The cleaning step in accordance with the present invention may consist of wiping, mechanical polishing, chemical cleaning in HF—HNO$_3$, dipping in ethanol or perchloric acid-butanol-methanol solution or any other laboratory standard cleaning procedures.

More particularly, the deoxidation step of the process in accordance with the present invention, is a chemical cleaning in HF—HNO$_3$ with a 2:1 volume ratio of HF (48% aqueous) with concentrated HNO$_3$ followed by a potentiostatic electrochemical polishing in a perchloric acid-butanol-methanol solution in a 1:12:7 ratio by volume, which may be effected by scanning from about 0 to 40 V at 7 mV/s for a titanium implant.

More particularly, the chemical cleaning step of the process in accordance with the present invention, is effected with a solution of H$_2$O$_2$ and H$_2$SO$_4$, HF and HNO$_3$, or H$_2$O$_2$ and KOH.

The preferred H$_2$O$_2$/H$_2$SO$_4$ solution has a 1:1 volume ratio of H$_2$O$_2$ (30%) with concentrated H$_2$SO$_4$.

The preferred HF/HNO$_3$ solution has a 1:2 volume ratio of HF (48% aqueous) with concentrated HNO$_3$.

The preferred H$_2$O$_2$/KOH solution has a 1:1 volume ratio of H$_2$O$_2$ (30%) with 40% aqueous KOH.

More particularly, the chemical cleaning step of the process in accordance with the present invention is conducted for about 2 hours at room temperature. It can be followed by a rinsing step in water.

The deoxidation of the implant surface permits bonding to metal atoms, and re-oxidation of the implant surface in a controlled manner permits bonding to oxygen.

More particularly, the re-oxidation step of the process in accordance with the present invention is effected at about 6 V in a phosphate buffer, such as NaH$_2$PO$_4$/Na$_2$HPO$_4$ in a 0.1:0.1M ratio.

DETAILED DESCRIPTION OF THE INVENTION

The bioactive conjugates of the present invention, once coated on an implant, provide the attachment through a bridge of biologically active molecules which promote tissue growth, stabilization and integration at the tissue-implant interface, and also provide a protection against reaction of the implant.

Further, the bioactive conjugates of the present invention also provide for a flexible and resilient coating on the implant which serves to absorb the forces applied on the implant and which may help prevent lesions and fractures of the tissue at the tissue-implant interface.

The bioactive conjugates also provide for a better attachment of the implant at soft tissue (epithelial cells) or hard tissue (bone) site.

Figure 1:
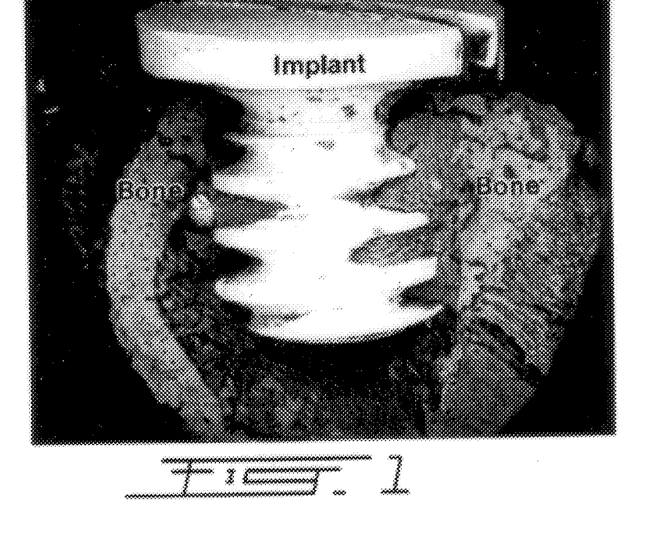
FIG. 1 is a scanning electron micrograph of a titanium screw implant in situ in a rat tibia bone model.

FIG. 1 illustrates the tissue-implant interface of a non-coated implant in situ in bone.

Figure 2:
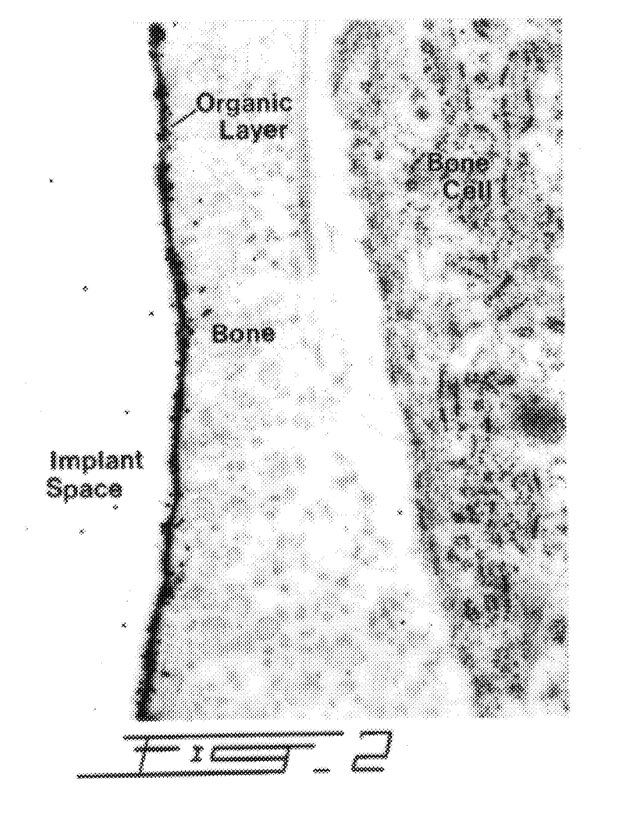
FIG. 2 is a transmission electron micrograph of the tissue-implant interface in a tibial bone showing an accumulation of organic material immunolabeled for the bone protein osteopontin.

A line at the bone-implant interface, can be observed at higher magnification by electron microscopy in FIG. 2, which was identified as containing a naturally occurring bone protein known as "osteopontin". Thereafter, in accordance with the present invention the preferred protein for coating an implant is osteopontin.

Figure 9A:
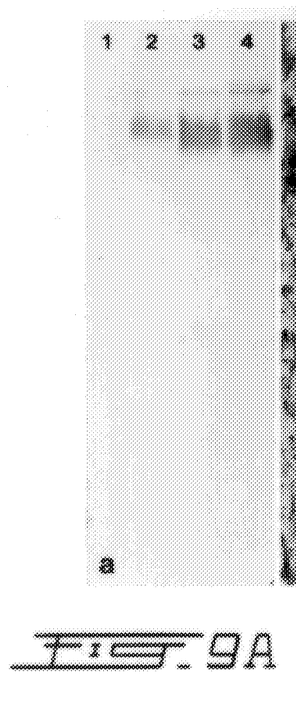
FIG. 9A illustrates an immunoblot with a polyclonal anti-osteopontin antibody raised in chickens and purified from egg yolks.

FIG. 9A illustrates immunoblot with an antibody against osteopontin raised in chickens and purified from egg yolk. The polyclonal anti-osteopontin antibody was raised against osteopontin purified from rat bone. Lane 1, rat serum albumin; Lane 2, total HCl/guanidine bone extract; Lane 3, purified rat bone osteopontin; Lane 4, purified rat bone osteopontin donated by Drs. M. C. Farach-Carson and W. T. Butler (University of Texas, Houston).

Figure 9B:
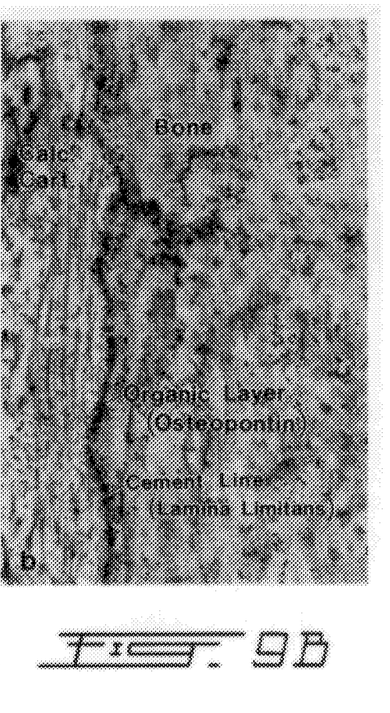
FIG. 9B illustrates immunocytochemical labeling for rat osteopontin at the interface between calcified cartilage and bone in the rat tibial growth plate using the same anti-osteopontin antibody as used for FIG. 9A.

FIG. 9B illustrates immunocytochemical labeling for rat osteopontin in the rat tibia using the anti-osteopontin antibody and demonstrating the concentration of this protein, as visualized by the accumulation of gold particles over an organic layer, referred to as the "cement line" or "lamina limitans", at a natural, matrix-matrix (calcified cartilage-bone) interface as found in normal tissues (McKee et al., Anat. Rec., 234:479–492, 1992; McKee et al., J. Bone Miner. Res., 8:485–496, 1992).

This interface represents the junction between two spatio-temporally distinct matrices created during normal long bone growth where bone is deposited by osteoblasts onto a "scaffolding" of calcified cartilage. During bone remodeling, this same layer of protein is also found at bone-bone interfaces ("cement lines"). It is thus proposed that osteoblasts behave similarly when encountering a titanium "substrate" and secrete an osteopontin-containing, organic layer at the bone-titanium interface (FIG. 10);

FIG. 10 illustrates that when a tooth erupts into the oral cavity, part of the reduced enamel organ is believed to fuse with the gingiva to form the functional epithelium (Schroeder and Listgarten, Monographs in Developmental Biology, Ed. A. Wolsky, Tarrytown, N.Y., Vol.2:1–127, 1971). More specifically, the "basal lamina" separating the maturation stage ameloblasts from the enamel surface shows characteristics similar to the internal basal lamina of the junctional epithelium, and may indeed take part in the formation of the initial epithelial attachment (Nanci et al., Histochemistry, 99:321–331, 1993).

Maturation stage ameloblasts are post-secretory cells which produce little or no enamel proteins, and indeed, the basal lamina separating them from enamel does not seem to contain much of these proteins. However, it is well known that under certain conditions (epithelial pearls; intermediate cementum), epithelial cells related to tooth formation can be reactivated to produce enamel proteins.

Consistent with the epithelial origin of the attachment, cells of the junctional epithelium were examined to determine whether they are able to express enamel proteins. Enamel proteins consist essentially of two classes of proteins, amelogenins and non-amelogenins (enamelins) both of which undergo substantial extracellular processing (reviewed in Nanci and Smith, Calcification in Biological Systems, Chapter 13: 313–343, 1992).

Figure 10A:
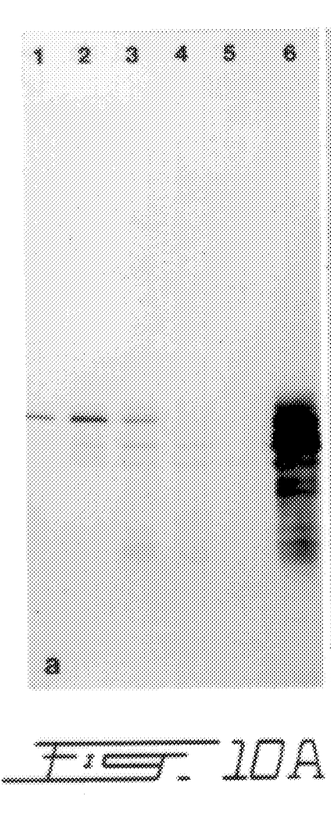
FIG. 10A is an immunoblot of intact proteins and degradation products in enamel organ and enamel matrix using rabbit anti-mouse amelogenin antibody.

An antibody raised in rabbits against recombinant mouse amelogenin protein expressed in E. coli (courtesy of the laboratory of Dr. H. C. Slavkin, Center for Craniofacial Molecular Biology, University of Southern California) was used to immunolocalize enamel proteins. Recently, proteins from rat incisor enamel were purified and antibodies to these proteins were raised in the chicken (purified from the egg yolk; in collaboration with Dr. C. E. Smith, McGill University). The rabbit anti-mouse amelogenin recognizes intact proteins and degradation products found between 14 and 31 kDa in ameloblasts (FIG. 10A, lanes 1–5) and enamel matrix (FIG. 10A, lane 6). Maturation stage ameloblasts (FIG. 10A, lanes 3–5) gradually stop producing enamel proteins.

Figure 10B:
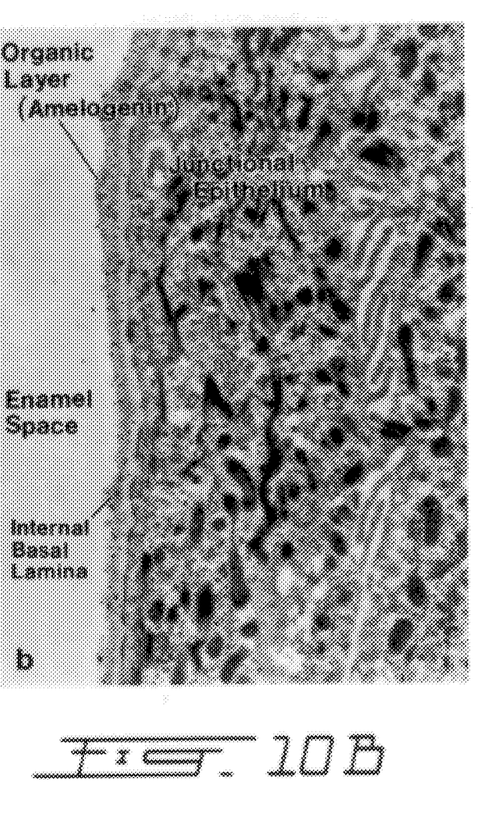
FIG. 10B illustrates the immunodetection of enamel proteins in the organic layer between the tooth surface and the junctional epithelium of rat molars.

Enamel proteins are immunodetected in the organic layer (internal basal lamina) between the tooth surface and the junctional epithelium of rat molars (FIG. 10B). Since so far it has not been possible to clearly demonstrate the presence of typical basement membrane constituents in the internal basal lamina of the junctional epithelium, or as a matter of fact of in that related to maturation stage ameloblasts, the possibility exists that these basal laminae represent extracellular matrices related to basement membranes but with a distinct composition reflecting their specialized function, such as mediating cell differentiation and/or promoting soft tissue-hard tissue adhesion.

In accordance with the present invention, it is proposed to use components of the internal basal lamina, and in particular enamel proteins, as a surface coating on the transgingival portion of titanium implants to promote cell differentiation and the formation of a functional and stable epithelial seal around the implant.

The process, in accordance with the present invention for coating a metal implant with a bioactive conjugate, comprises the following steps.

First, a metal implant surface is cleaned and, in addition, may be deoxidized by effecting a potentiostatic electrochemical polishing in a perchloric acid-butanol-methanol solution similar to that described by M. Volmer-Uebing et al. (*Applied Surface Science,* 55:19–35, 1992). The preparation of low-oxide metal surfaces at room temperature is by polarizing the metal in 1M perchloric acid ($HClO_4$) at a potential of 40V. Under these conditions the metal is in a thermodynamically stable phase. The deoxidized surface may then be reoxidized also by potentiostatic electrochemical polarization in a phosphate buffer at 6 V.

Second, the cleaned and deoxidized, or cleaned, deoxidized and controlled re-oxidized implant surface is contacted with compounds that cause covalent coating with a bioactive conjugate of the present invention.

Theoretical Coverage of Surface With Sulfur
a) Perfect Crystal (Flat Surface)

The surface concentration of titanium (Ti) is about $1.6 \times 10^{15}$ atoms/$cm^2$ and the diameter of sulfur (S) is about 2× diameter of Ti, thus the surface concentration of sulfur atoms is about $0.8 \times 10^{15}$ atoms/$cm^2$ and each sulfur atom is attached to a chain of 18 carbon atoms of about 15 Å long.

Because the depth analyzed is 45 Å, the surface concentration of carbon atoms is about $1.4 \times 10^{16}$ atoms/$cm^2$, that is about 18 times the surface concentration of sulfur atoms).

Depth probed ($\approx$45 Å)–length of thiolase ($\approx$15 Å)=30 Å

30 Å Ti$\approx$11 monolayers$\approx 1.8 \times 10^{16}$ atoms/$cm_2$

Ti:S:C=$1.8 \times 10^{16}$:$0.8 \times 10^{15}$:$1.4 \times 10^{16}$=54.9%:2.4%:42.7% b) 45° Sawtooth Surface (Rough Surface, More Realistic)

Ti:S:C=41.6%:2.8%:55.6% c) Contaminated Surface

Since titanium (Ti) is a reactive metal, it is difficult to clean same and it gets contaminated easily.

The realistic coverage of the Ti surface with S is <2.8%, this value depending on the extent of the contamination of the surface.

TABLE 1

Atomic percentages at reduced titanium surfaces
following treatment with a functionalized alkanethiol

| Treatment | O | Ti | C | S |
|---|---|---|---|---|
| $SH(CH_2)_2COOH$ | 35.7 | 7.3 | 53.9 | 2.1 |
| $SH(CH_2)_2COOH/H_2O$ | 43.2 | 15.4 | 37.2 | 2 |

Table 1 above provides a comparison of chemically-treated reduced titanium surfaces before and after aqueous exposure.

Figure 11:
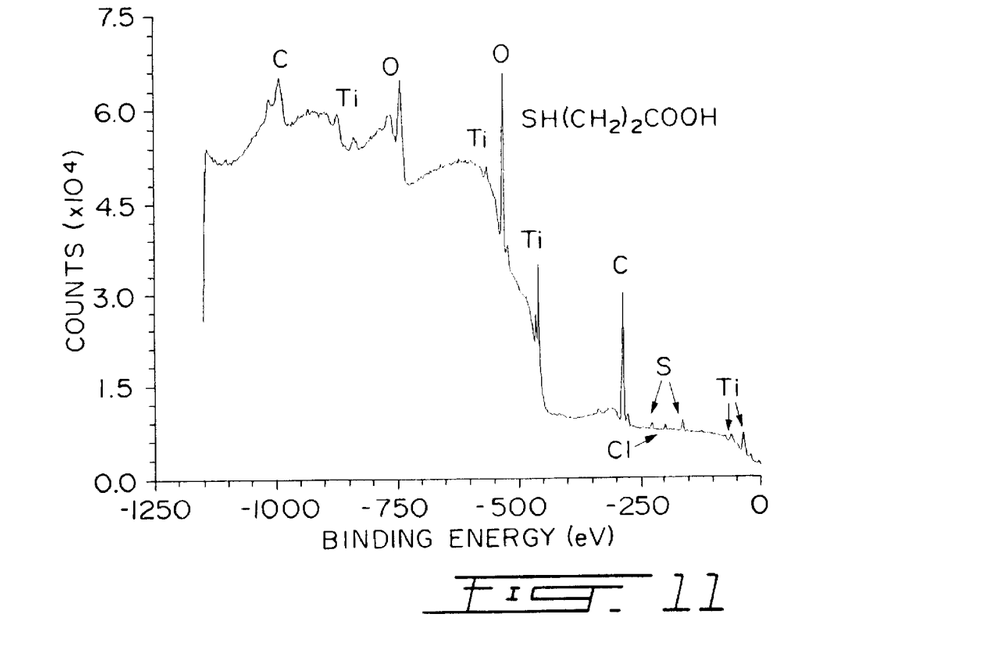
FIG. 11 is an XPS spectrum showing the presence of sulfur at the titanium reduced surface of the treatment with a functionalized short-chain alkanethiol.

FIG. 11 demonstrates sulfur peaks indicating thiol binding to titanium.

Figure 12:
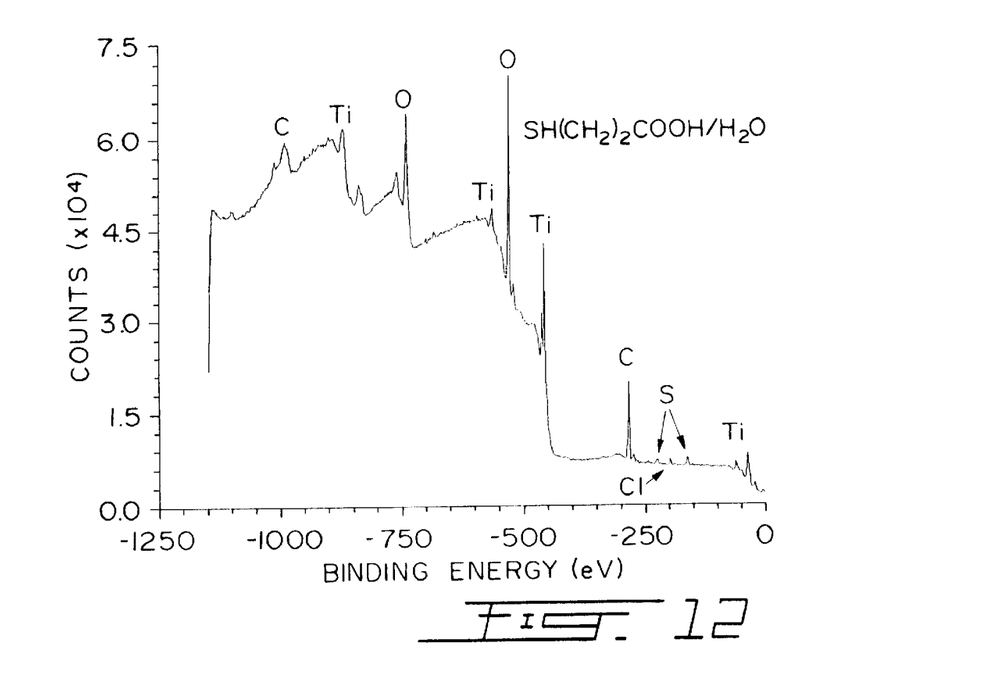
FIG. 12 is an XPS spectrum showing retention of sulfur and stability of the Ti—S bonding following exposure of the alkane-treated titanium surface to water.

FIG. 12 shows no major change in the sulfur (thiol) peaks after aqueous treatment.

The present invention will be more readily understood by referring to the following examples which are given to illustrate the invention rather than to limit its scope.

EXAMPLE I

Coating of a Titanium Implant With Octadecyl Thiolate

Sample Preparation

The titanium metal substrate is cleaned by mechanical polishing with alumina 0.1 um followed by an ultrasonic chemical cleaning in pure acetone for about 15 min. The substrate is electrochemically polished in a perchloric acid-butanol-methanol solution in a 1:12:7 ratio by volume for 30 min. at about 40 V. This technique establishes the electrochemical conditions at which the surface contaminants are unstable and are removed. While we have not attempted to optimize the experimental conditions, the technique, as used, causes a measurable cleaning of the titanium surface.

This is carried out in a $N_2$-flushed dry box which also contains $10^{-3}$ to $10^{-4}$M hexane solutions of octadecyl thiol, $CH_3$—$(CH_2)_{17}$—$SH$. Thus, without exposure to air, which is capable of re-contaminating the highly reactive clean titanium surface, the metal is submerged in the thiol solution overnight. This permits the thiol to react with the metal surface, forming self-assembling monolayers, such as which extend above the metal surface by about 15 Angstroms. Samples were rinsed in hexane before analysis.

Analysis Technique

The surface analytical technique used is called X-ray Photoelectron Spectroscopy (XPS) or Electron Spectroscopy for Chemical Analysis (ESCA). It has the advantage that small differences in electron density at the emitting atom, caused by differences in chemical bonding, are reflected in small shifts in the energy of the emitted electron. Software has been developed which permits the computer manipulation of these data, allowing the separation of close-lying peaks for further study.

The depth probed at the titanium emission energy is about 45 Angstroms; for a perfectly flat titanium crystal covered with a monolayer of thiol, the depth probed into the titanium is, then, about 30 Angstroms. For a rougher surface, modeled on a 45° saw-tooth, this depth is closer to 20 Angstroms although the full thiolate monolayer is probed in both cases.

Results and Discussion

Figure 3:
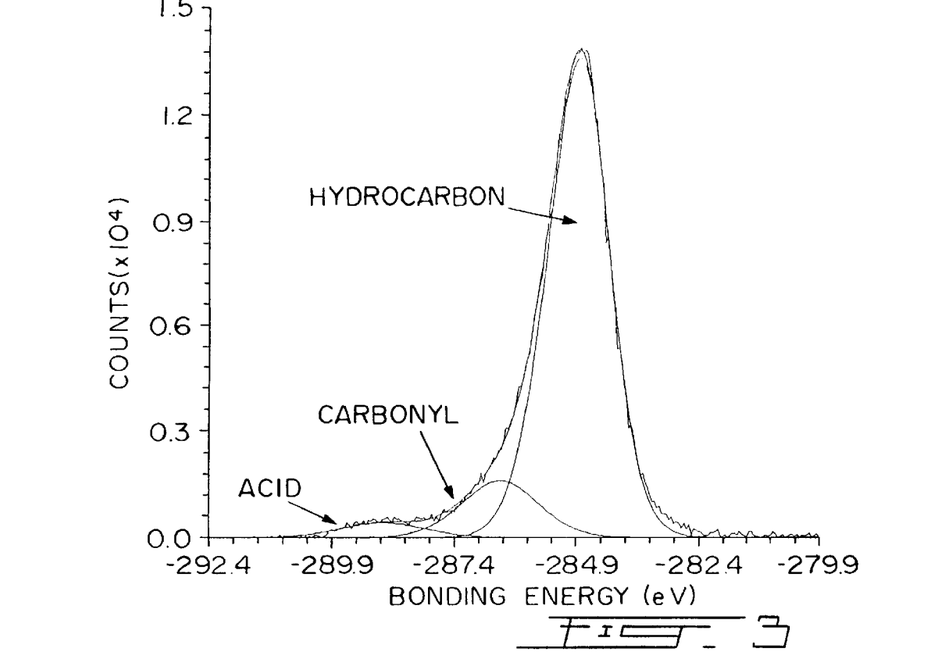
FIG. 3 represents the carbon spectrum obtained by X-ray Photoelectron Spectroscopy of the surface of a titanium implant which has reacted with a hexane solution of octadecyl thiol, showing the octadecyl thiolate attached thereto.
Figure 4:
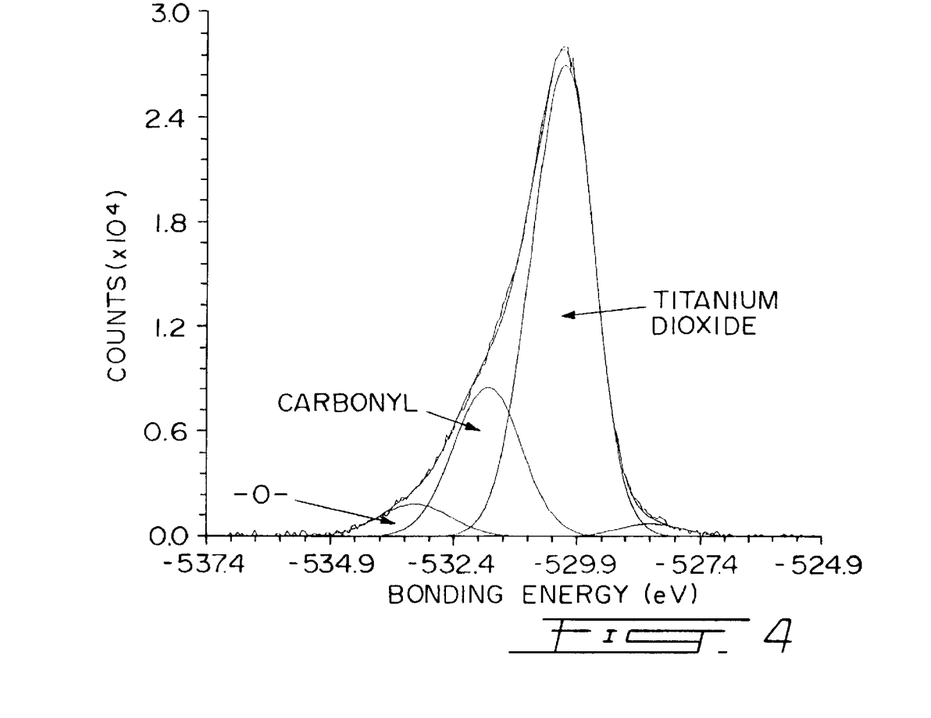
FIG. 4 represents the oxygen spectrum obtained by X-ray Photoelectron Spectroscopy of the surface of a titanium implant with octadecyl thiolate attached thereto.
Figure 5:
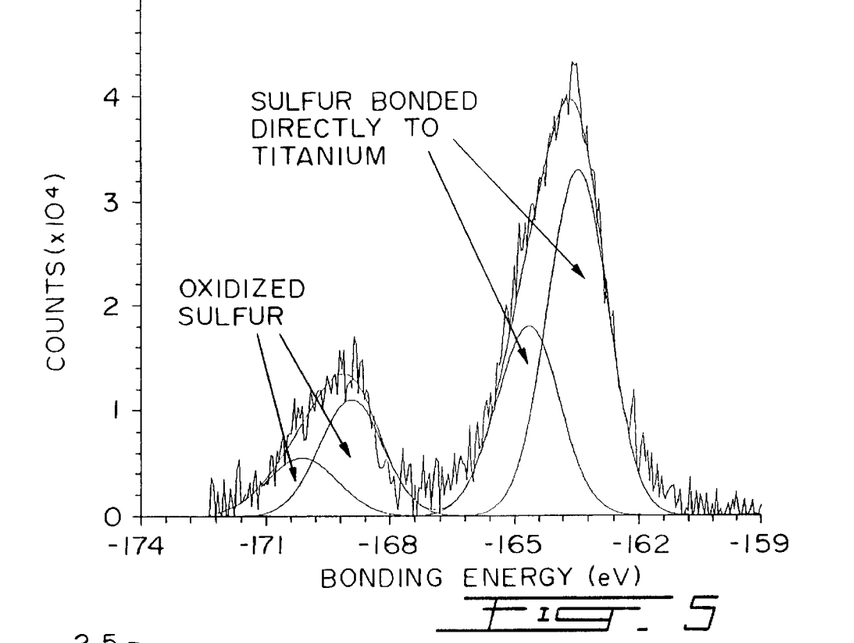
FIG. 5 represents the sulfur spectrum obtained by X-ray Photoelectron Spectroscopy of the surface of a titanium implant with octadecyl thiolate attached thereto.
Figure 6:
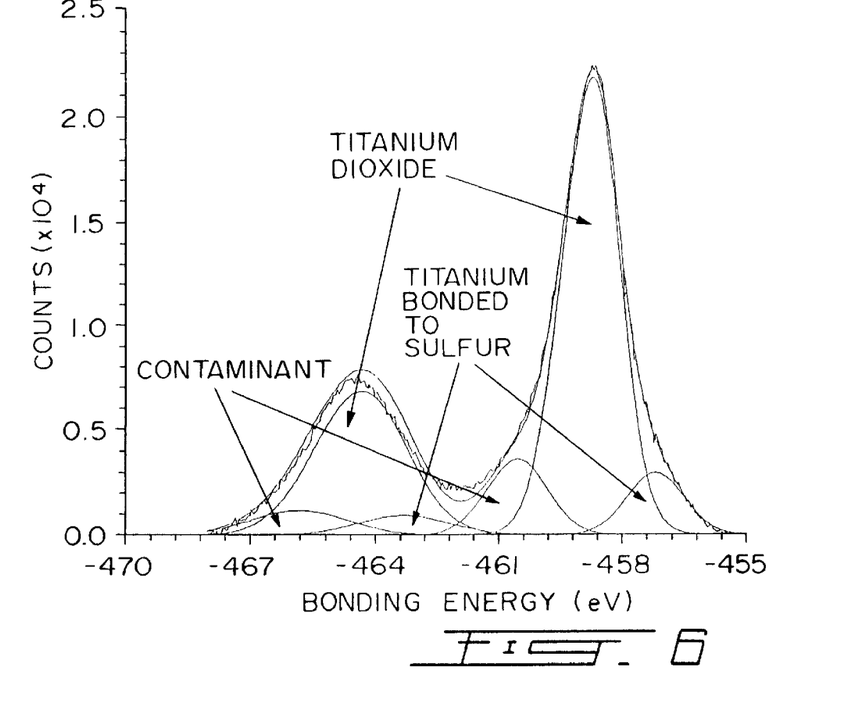
FIG. 6 represents the titanium spectrum obtained by X-ray Photoelectron Spectroscopy of the surface of a titanium implant with octadecyl thiolate attached thereto.

A typical set of spectra is seen in the accompanying FIGS. 3 to 6, where FIG. 3 is the carbon spectrum, FIG. 4 is the oxygen spectrum, FIG. 5 is the sulfur spectrum and FIG. 6 is the titanium spectrum. The peaks for carbon and oxygen arise from electrons emitted from s-type orbitals, meaning that each peak indicates another environment. Their probable attributions are indicated on the FIGS. 3 and 4.

On the other hand, the peaks for sulfur and titanium arise from electrons emitted from p-type orbitals, meaning that pairs of peaks indicate different environments. Again, probable attributions are indicated on the FIGS. 5 and 6.

The fact that titanium can clearly be detected indicates that only a monolayer of thiol was deposited. Variations in carbon and oxygen percentages, as well as in the various titanium components, indicate some point-to-point variability in cleaning and thiol deposition. However, the thiol directly bonded to titanium appears impervious to attack by water vapor and by direct water immersion for 2.5 hour.

EXAMPLE II

Covalent Attachment of Alkaline Phosphatase to a Titanium Implant

A cleaned titanium implant is coated with 16-aminohexadecanethiol by the general procedure described in Example I. The implant is then stirred for 60 min. at 25° C. under $N_2$ with a solution of glutaraldehyde in 0.1M phosphate buffer. The implant is then rinsed with buffer and stirred for 12 h at 25° C. with a solution of 3 mg alkaline phosphatase (from bovine intestinal mucosa, 5 units/mg) in 3 mL phosphate buffer. The implant is then rinsed with buffer. Enzymatic activity should be measured by the method of Lowry et al. (*J. Biol. Chem.,* 164:321, 1946).

EXAMPLE III

Covalent Attachment of Alkaline Phosphatase to a Titanium Implant

A titanium implant was cleaned by the general procedure of Example I and subjected to controlled re-oxidation. The implant was then stirred for 2 h under $N_2$ with a 10% solution of 3-aminopropyltriethoxysilane in refluxing toluene. The modified implant was then covalently coupled with alkaline phosphatase by the glutaraldehyde procedure described in Example II. Enzymatic activity was measured by the method of Lowry et al. (*J. Biol. Chem.,* 164:321, 1946).

Figure 7:
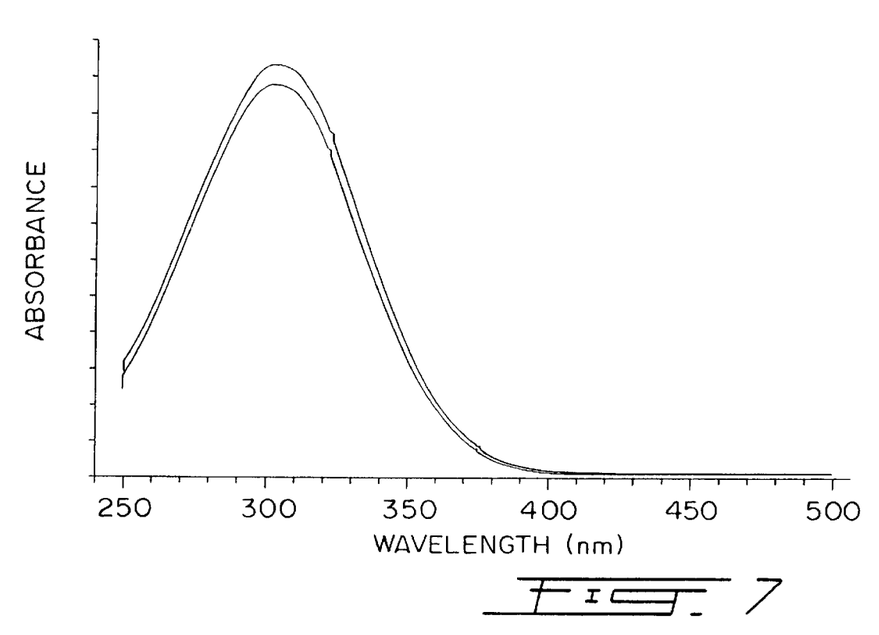
FIG. 7 is a UV spectrum showing initial evidence of the biological activity of a bioactive conjugate coating an implant prepared according to the present invention.
Figure 8:
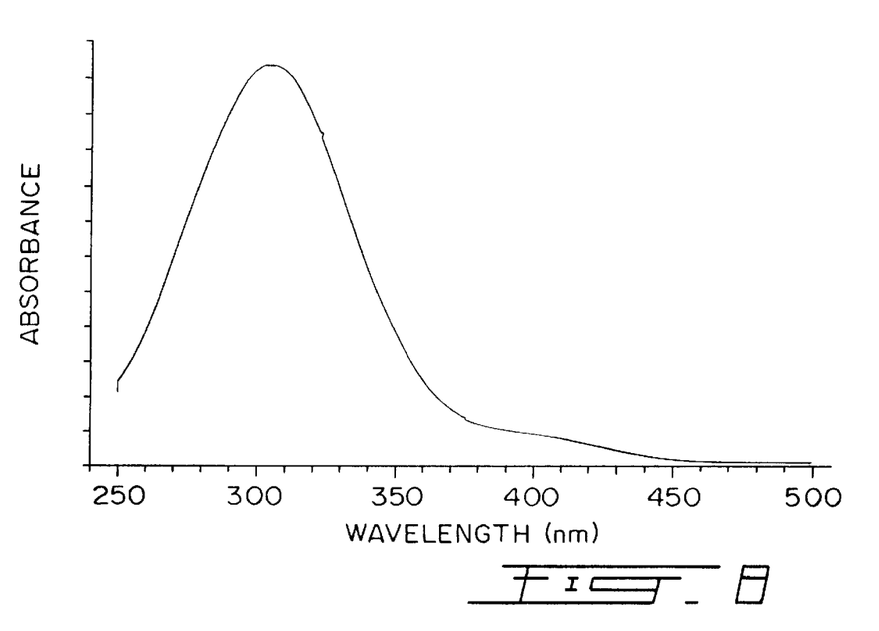
FIG. 8 is a UV spectrum showing evidence of the biological activity of the bioactive conjugate coating the implant after 14 hours of incubation.

FIG. 8 shows the appearance of a peak at 405 nm which provides clear evidence the alkaline phosphatase covalently attached to the implant surface has retained its biological activity after 14 hours of incubation. Although the peak near 400 nm is essentially absent from FIG. 7, which is taken near the beginning of the reaction, weak absorbance near 400 nm indicates initial stages of formation of p-nitrophenol by enzyme-catalysed hydrolysis.

EXAMPLE IV

Covalent Attachment of Alkaline Phosphatase to $TiO_2$

A sample of powdered $TiO_2$ equivalent in weight to that of a standard titanium implant was stirred for 2 h under $N_2$ with a 10% solution of 3-aminopropyltriethoxysilane in refluxing toluene. After centrifugation, rinsing with toluene, and drying, the modified $TiO_2$ was stirred for 60 min. at 25° C. under $N_2$ with a 2.5% solution of glutaraldehyde in 0.1M phosphate buffer.

After centrifugation and rinsing with 0.1M buffer, the modified $TiO_2$ was stirred for 12 h. at 25° C. with a solution of 3 mg alkaline phosphatase (from bovine intestinal mucosa, 5 units/mg) in 3 mL phosphate buffer. The modified $TiO_2$ was then rinsed thoroughly with buffer, and its enzymatic activity was measured by the method of Lowry et al. (*J. Biol. Chem.,* 164:321, 1946).

Figure 13:
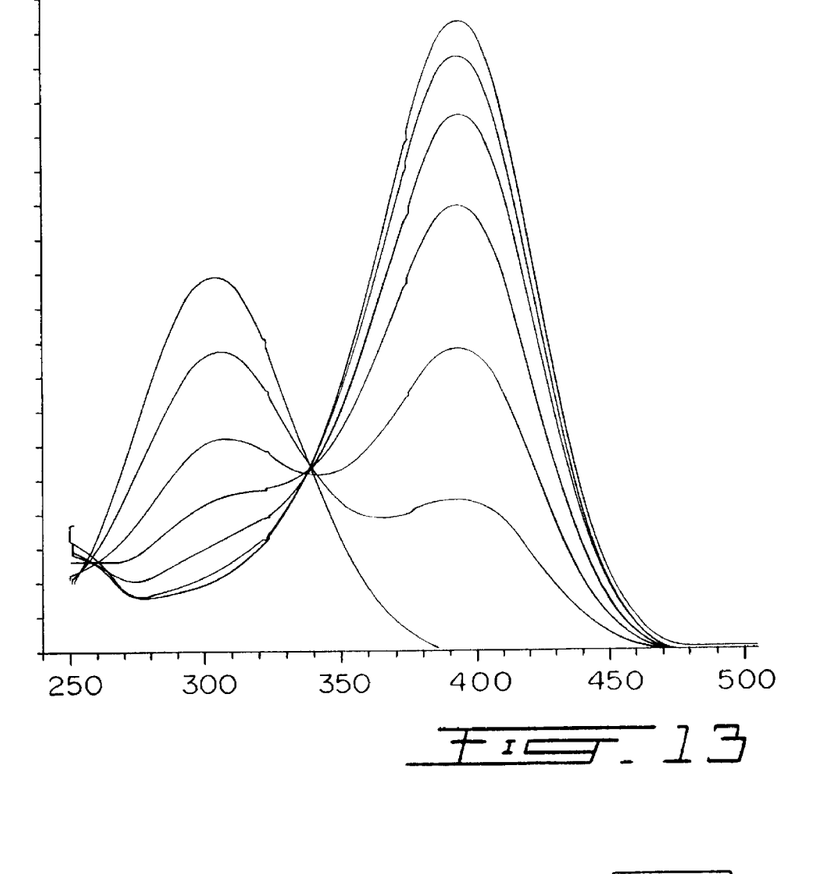
FIG. 13 represents a series of seven UV spectra of the surface of a titanium implant with alkaline phosphatase attached thereto.

FIG. 13 shows a series of seven UV spectra taken at 15 min. intervals from t=0 to t=90 min. during the course of an assay of a sample of modified $TiO_2$ using the method of Lowry. The peak near 305 nm, which corresponds to unhydrolyzed p-nitrophenyl phosphate, decreases continuously and is essentially absent at t=90 min. There is a corresponding increase in absorption near 400 nm, which corresponds to the formation of p-nitrophenolate. These spectra provide clear evidence for covalent attachment of alkaline phosphatase to $TiO_2$ in an enzymatically active form.

Figure 14A:
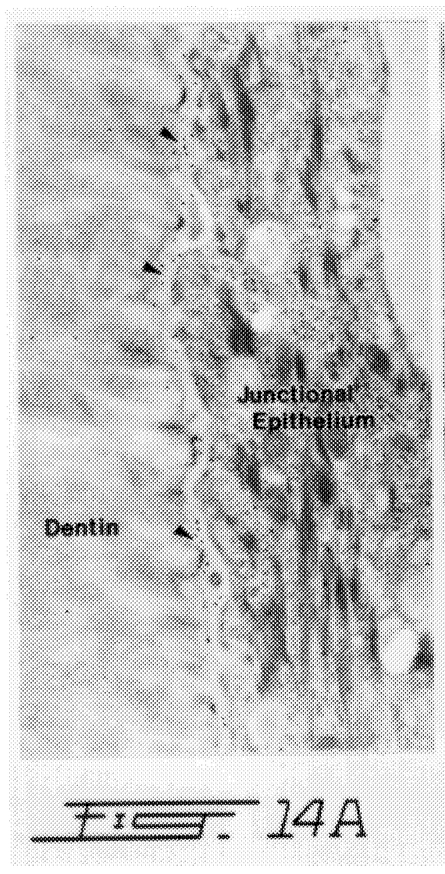
FIG. 14A illustrates a junctional epithelial cell in contact with surgically-exposed dentin showing the presence of enamel proteins (gold particles, arrowheads) interposed between the cell and the exposed dentin.
Figure 14B:
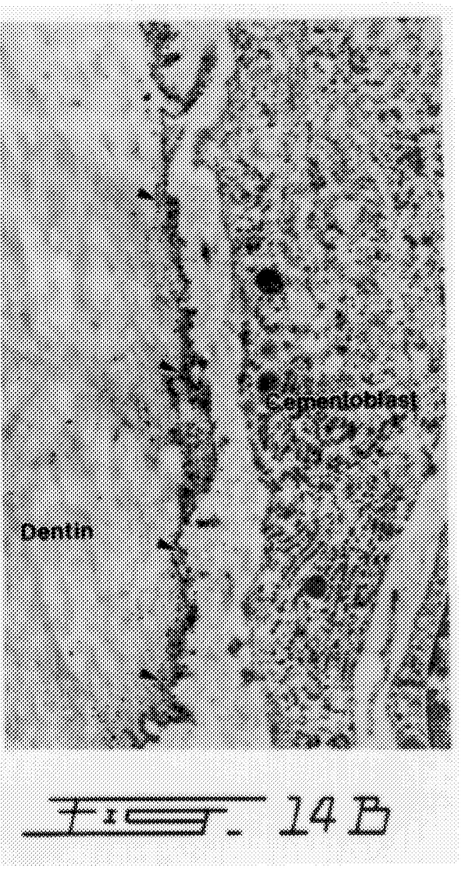
FIG. 14B is a micrograph illustrating a layer of osteopontin (gold particles, arrowheads) separating exposed dentin and a (pre)cementoblast.

For examining tissue repair and the production of new proteins at exposed mineralized tissue surfaces, we have used a model where the junctional epithelium is surgically detached (reflected) from the tooth surface, and the palatal root of rat molars is exposed, and the cementum and outermost dentin is removed from the root surface with a dental bur. Tissue healing in this circumstance occurs soon thereafter and comprises both a soft and hard tissue response in which two principal events occur. Firstly, junctional epithelium migrates down the tooth and over the damaged root surface and re-establishes an epithelial attachment. Coincident with the contact of these epithelial cells to the exposed dentin and/or cementum, enamel proteins (as indicated by immunoreactivity to antibodies raised against this epithelial secretory product) are secreted and accumulate as an organic layer at the root surface (FIG. 14A) adjacent to junctional epithelial cells. This class of protein is generally not believed to be expressed after completion of the enamel layer in unerupted teeth yet has here been shown to be part of the normal epithelial attachment (see FIG. 10B) and to be produced during reparation of this epithelial structure. Secondly, with regard to hard tissue formation and healing at these damaged sites in regions more apical to the epithelial cell migration, (pre)cementoblasts are found against the tooth surface and are associated with the appearance of a layer of osteopontin (FIG. 14B) at the exposed root surface. This organic coating of osteopontin appears to be the initial event of reparative cementogenesis in which typical cementum then begins to fill in the defect at the root surface.

Figure 15:
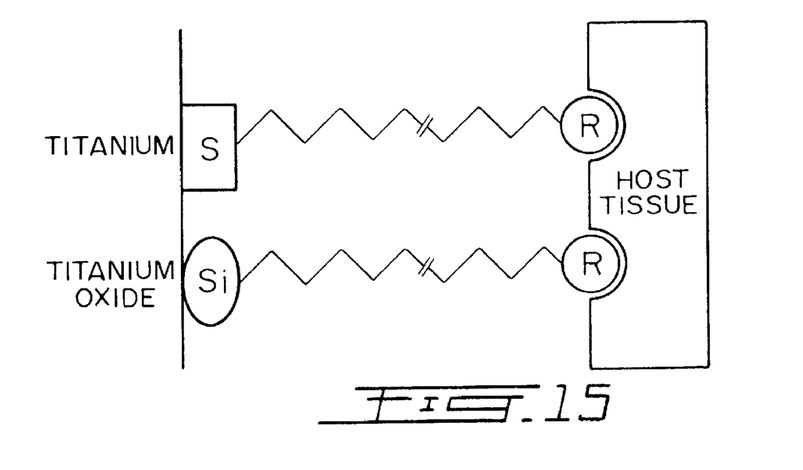
FIG. 15 is a scheme of a titanium surface implant coated in accordance with the present invention.

FIG. 15 is a scheme of a titanium surface implant coated in accordance with the present invention shown in epithelial attachment.

EXAMPLE V

Covalent Attachment of 11-(triethoxysilyl)-1-undecanamine to Ti Surface 11-(Triethoxysilyl)-1-undecanamine is synthesized from commercially available 11-undecenoic acid in four steps. The corresponding acid is converted into the acid acid chloride and then into the corresponding amide, which is reduced by $LiAlH_4$ to give 11-undecenamine. Direct Silylation using triethoxysilane and $H_2PtCl_6$ as a catalyst, followed by ethanolysis and distillation provides 11-(triethoxysilyl)-1-undecanamine.

The titanium surfaces to be modified are cleaned by treating same in a $H_2SO_4/H_2O_2$ solution with a volume ratio of 50:50 of concentrated $H_2SO_4$ and 30% $H_2O_2$.

The 11-(triethoxysilyl)-1-undecanamine compound is used to covalently modify cleaned titanium surfaces according to the procedure set forth in Example III.

The 11-(triethoxysilyl)-1-undecanamine-modified titanium surfaces are more resistant to hydrolysis than surfaces modified by monodentate silylamine.

EXAMPLE VI

Covalent Attachment of N,N-bis(2-propenyl)-1,3-propanediamine or bis(silyl)amine to Ti Surface N,N-bis(2-propenyl)-1,3-propanediamine is prepared by the addition of diallylamine to acrylonitrile, followed by a reduction with $LiAlH_4$.

The titanium surfaces to be modified are previously cleaned by treating same in a $H_2SO_4/H_2O_2$ solution with a volume ratio of 50:50 of concentrated $H_2SO_4$ and 30% $H_2O_2$.

The N,N-bis(2-propenyl)-1,3-propanediamine compound is converted by direct hydrosilylation into bis(silyl)amine, which provides two anchoring points for covalent attachment to a titanium surface.

Then, the bis(silyl)amine is used to covalently modify cleaned titanium surfaces according to the procedure set forth in Example III.

The bis(silyl)amine-modified titanium surfaces are more resistant to hydrolysis than surfaces modified by monodentate silylamine.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A process for covalently coating a titanium implant with a bioactive conjugate, which comprises the steps of:
   a) chemically cleaning a titanium implant surface by electrochemical deoxidation in a solution selected from the group consisting of ethanol, perchloric acid-butanol-methanol, $H_2O_2$—NaCl—$NaH_2PO_4$; and
   b) without exposure to air, coating the cleaned titanium implant surface from step a) to form a covalently attached bioactive thiolate conjugate layer, wherein said thiolate conjugate has the following structural formula I:

$$—R—X—P \qquad\qquad I$$

wherein
   R is S covalently attached to the titanium implant surface;
   X is a linker covalently attached to R and selected from a bond, linear or branched chains of 1 to 30 covalently attached atoms of at least one of C, N, O, Si or S, rings of at least one of C, N, O, Si or S, and a combination thereof, and
   P is a covalently attached bioactive molecule moiety which promotes tissue growth, stabilization or integration;

and wherein said bioactive moiety retains its biological activity.

2. A process according to claim 1, wherein the linker X terminates in an amino group and is covalently bonded to the bioactive moiety P through reaction with glutaraldehyde.

3. A process according to claim 1, wherein the electrochemical deoxidation is effected at about 40V for 30 minutes.

4. A process according to claim 1, wherein the covalently attached bioactive molecule moiety is selected from the group consisting of $\alpha_2$HS-glycoprotein and fibronectin.

5. A process according to claim 1, wherein the covalently attached bioactive molecule moiety is selected from the group consisting of osteopontin, bone sialoprotein, bone acidic glycoprotein-75, osteocalcin, osteonectin, bone morphogenetic proteins, transforming growth factors, laminin, type IV collagen, type VIII collagen, enamel proteins, cell adhesion peptides, prostaglandin, serum proteins, glucocorticosteroids, phosphoserine, pyrophosphates, phosphothreonine, phosvitin, phosphophoryn, phosphonates, phosphatases, bone and epithelial proteoglycans, and mineral binding peptide sequences.

6. A process according to claim 5, wherein the covalently attached bioactive moiety is selected from the group consisting of osteopontin and bone morphogenetic proteins.

7. A process according to claim 5, wherein the covalently attached bioactive moiety is selected from the group consisting of amelogenins and non-amelogenins.

8. A process according to claim 5, wherein the covalently attached bioactive moiety is a biphosphonate.

9. A process according to claim 5, wherein the covalently attached bioactive moiety is a cell adhesion peptide.

10. A process according to claim 5, wherein the covalently attached bioactive moiety is a peptide sequence selected from the group consisting of arginine-glycine-aspartic acid and polyaspartate.

11. A process for covalently coating a titanium implant with a bioactive conjugate, which comprises the steps of:
   a) chemically cleaning a titanium implant surface by
      i) electrochemical deoxidation in a solution selected from the group consisting of ethanol, perchloric acid-butanol-methanol, $H_2O_2$—NaCl—$NaH_2PO_4$, and subsequent controlled electrochemical reoxidation; or
      ii) chemical oxidation with a solution selected from the group consisting of $HF/HNO_3$, $H_2O_2/H_2SO_4$ and $H_2O_2/KOH$; and
   b) under an inert atmosphere, coating the cleaned titanium implant surface of step a) to form a covalently attached bioactive siloxane conjugate layer, wherein said siloxane conjugate has the following structural Formula I:

$$—R—X—P \qquad\qquad I$$

wherein,
   R is O covalently attached to the titanium implant surface;
   X is a linker containing Si covalently attached to R and selected from linear or branched chains of 1 to 30 covalently attached atoms of at least C, N, O, Si or S, rings of at least one of C, N, O, Si or S, and a combination thereof; and
   P is a bioactive molecule moiety stably attached to X via a covalent bond; said bioactive molecule moiety promoting tissue growth, stabilization or integration;

and wherein said bioactive moiety retains its biological activity.

12. A process according to claim 11, wherein the linker X terminates in an amino group and is covalently bonded to the bioactive moiety P through reaction with glutaraldehyde.

13. A process according to claim 11, wherein the covalently attached bioactive molecule moiety is selected from the group consisting of $\alpha_2$HS-glycoprotein and fibronectin.

14. A process according to claim 11, wherein the covalently attached bioactive molecule moiety is selected from the group consisting of osteopontin, bone sialoprotein, bone acidic glycoprotein-75, osteocalcin, osteonectin, bone morphogenetic proteins, transforming growth factors, laminin, type IV collagen, type VIII collagen, enamel proteins, cell adhesion peptides, prostaglandin, serum proteins, glucocorticosteriods, phosphoserine, pyrophosphates, phosphothreonine, phosvitin, phosphophoryn, phosphonates, phosphatases, bone and epithelial proteoglycans, and mineral binding peptide sequences.

15. A process according to claim 14, wherein the covalently attached bioactive moiety is selected from the group consisting of osteopontin and bone morphogenetic proteins.

16. A process according to claim 14, wherein the covalently attached bioactive moiety is selected from the group consisting of amelogenins and non-amelogenins.

17. A process according to claim 14, wherein the covalently attached bioactive moiety is a biphosphonate.

18. A process according to claim 14, wherein the covalently attached bioactive moiety is a cell adhesion peptide.

19. A process according to claim 14, wherein the covalently attached bioactive moiety is a peptide sequence selected from the group consisting of arginine-glycine-aspartic acid and polyaspartate.

* * * * *